United States Patent [19]

Boothe et al.

[11] 4,404,375
[45] Sep. 13, 1983

[54] CEPHALOSPORANIC ACID DERIVATIVES

[75] Inventors: James H. Boothe, Montvale, N.J.;
Adma S. Ross, Suffern, N.Y.

[73] Assignee: American Cyanamid Company, Stamford, Conn.

[21] Appl. No.: 367,501

[22] Filed: Apr. 12, 1982

Related U.S. Application Data

[62] Division of Ser. No. 145,071, Apr. 30, 1980, Pat. No. 4,336,375.

[51] Int. Cl.³ .................. C07D 501/36; A61K 31/545
[52] U.S. Cl. ........................ 544/27; 424/246
[58] Field of Search ............... 544/27, 21, 26; 424/246

[56] References Cited

U.S. PATENT DOCUMENTS

| | | | |
|---|---|---|---|
| 4,113,944 | 9/1978 | Kai et al. | 544/27 |
| 4,179,502 | 12/1979 | Numata et al. | 544/27 |
| 4,334,062 | 6/1982 | Curran | 544/27 |
| 4,336,375 | 6/1982 | Boothe et al. | 544/27 |
| 4,338,452 | 7/1982 | Katner et al. | 544/27 |

FOREIGN PATENT DOCUMENTS

| | | |
|---|---|---|
| 859384 | 10/1972 | Belgium. |
| 78/1433 | 2/1978 | South Africa. |
| 78/01870 | 3/1978 | South Africa. |

*Primary Examiner*—Nicholas S. Rizzo
*Attorney, Agent, or Firm*—Mary-Ellen M. Timbers

[57] ABSTRACT

7-acetamidocephalosporins are disclosed herein which are substituted at position 3 of the cephalosporin nucleus with the group

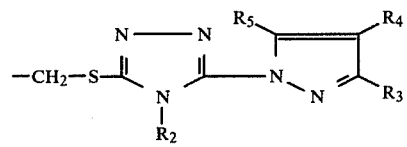

wherein $R_2$ is selected from the group hydrogen, amino, $C_1$ to $C_6$ alkylamino and di-$C_1$ to $C_6$ alkylamino and $R_3$, $R_4$ and $R_5$ are the same or different and are selected from the group hydrogen, hydroxy, $C_1$ to $C_6$ alkyl, $C_1$ to $C_6$ alkoxy, trifluoromethyl, phenyl, substituted phenyl, heterocyclic aryl, and $R_3$ and $R_4$ or $R_4$ and $R_5$ taken together are the moiety —$CH_2(CH_2)_2CH_2$—.

9 Claims, No Drawings

CEPHALOSPORANIC ACID DERIVATIVES

CROSS-REFERENCE TO RELATED APPLICATIONS

This application is a divisional of copending application Ser. No. 145,071, filed Apr. 30, 1980, now U.S. Pat. No. 4,336,375, issued June 22, 1982.

FIELD OF INVENTION

This invention is related to cephalosporanic acids, esters, amides and acid salts. More particularly, this invention is related to such cephalosporanic compounds having at the 3 position the group —$CH_2$—S— heterocyclic aryl.

DISCUSSION OF THE PRIOR ART

The prior art discloses a variety of cephalosporin compounds bearing at position 3 of the cephalosporin nucleus a —S— hetero group. For example, 3-S-heterocyclic cephalosporins have been studied where the 7-acyl side chain is substituted with benzyl or thienylmethyl, the heterocyclic moiety being the tetrazol, thiadrazole, or triazole type. See Irish Pat. No. 415/62; Derwent Basic No. 7,044 and Van Heyningen, E., (1967), Advan. Drug Res. 4, 1–70.

The subject is reviewed in the book "Structure-activity Relationships Among the Semisynthetic Antibiotics," edited by D. Perlman; the chapter by Weber and Ott, part G with its accompanying tables. However, 3-S-heterocyclics bearing a pyrazolyl-substituted 1,2,4-triazole have not been synthesized.

SUMMARY OF THE INVENTION

This invention is concerned with 3-S-heterocephalosporins of the formula

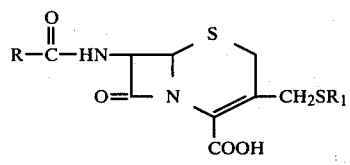

wherein R is selected from the group

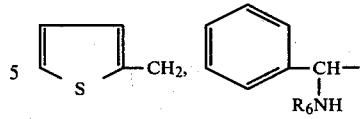

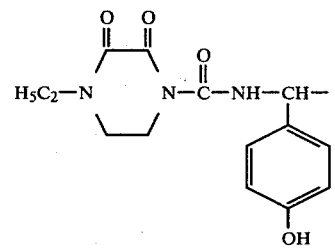  and

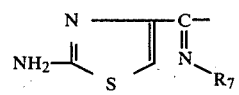

wherein $R_6$ is is hydrogen or $C_1$ to $C_6$ alkoxycarbonyl and $R_7$ is $C_1$ to $C_6$ alkoxy and $R_1$ is a moiety selected from the group of the formula

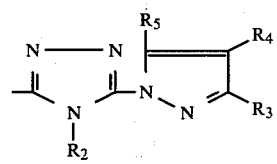

wherein $R_2$ is selected from the group hydrogen, amino, $C_1$ to $C_6$ alkylamino and di-$C_1$ to $C_6$ alkylamino; $R_3$, $R_4$ and $R_5$ are the same or different and are selected from the group hydrogen, hydroxy, $C_1$ to $C_6$ alkyl, $C_1$ to $C_6$ alkoxy, trifluoromethyl, phenyl, substituted phenyl, heterocyclic aryl, and $R_3$ and $R_4$ or $R_4$ and $R_5$ taken together are the moiety —$CH_2(CH_2)_2CH_2$—; and the pharmaceutically acceptable non-toxic salts thereof. The compounds are antibacterial agents active against Gram positive and negative bacteria.

The present invention further encompasses the process for the preparation of the compounds of formula I.

DESCRIPTION OF THE PREFERRED EMBODIMENTS

The compounds of the present invention are subgenerically represented by the following:

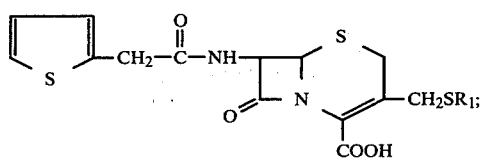

Ia

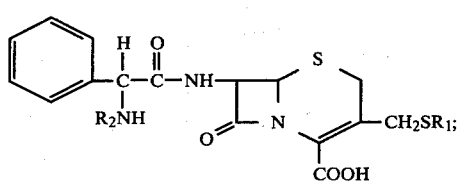

Ib

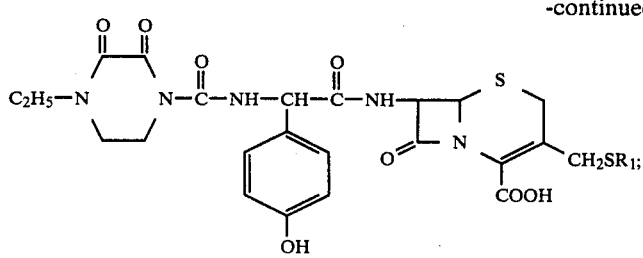

and

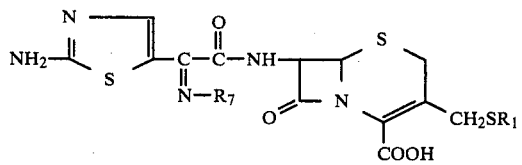

wherein $R_1$ is a moiety selected from the group of the formula

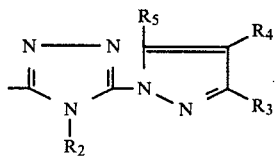

wherein $R_2$ is selected from the group hydrogen, amino, $C_1$ to $C_6$ alkylamino, and di-$C_1$ to $C_6$ alkylamino; $R_3$, $R_4$ and $R_5$ are the same or different and are selected from the group hydrogen, hydroxy, $C_1$ to $C_6$ alkyl, $C_1$ to $C_6$ alkoxy, trifluoromethyl, phenyl, substituted phenyl, heterocyclic aryl, and $R_3$ and $R_4$ or $R_4$ and $R_5$ taken together are the moiety —$CH_2(CH_2)_2CH_2$—; $R_6$ is hydrogen or $C_1$ to $C_6$ alkoxycarbonyl, and $R_7$ is $C_1$ to $C_6$ alkoxy, and the pharmaceutically acceptable salts thereof.

In the compounds of formula I, it is preferred that $R_3$, $R_4$ and $R_5$ are the same or different and are selected from the group hydrogen; $C_1$ to $C_3$ alkyl, for example methyl, ethyl, n-propyl or i-propyl; phenyl; phenyl substituted with mono- or di-methyl, methoxy, chloro, bromo or trifluormethyl; thienyl; and pyrroyl.

In the above preferred compounds when $R_3$, $R_4$ and $R_5$ are the same and are hydrogen, it is preferred that $R_2$ is selected from the group hydrogen and amino, most preferably amino.

In the above preferred compounds, when $R_3$, $R_4$ and $R_5$ are different, it is most preferred that such are selected from the group (on the pyrazol-1-yl nucleus) hydrogen, 3-methyl, 3-phenyl, 3-thien-2-yl, 3,5-dimethyl, 3-methyl-5-phenyl and 3-methyl-5-thien-2-yl. In such preferred and most preferred compounds, it is preferred that $R_2$ is selected from the group hydrogen and amino, most preferably amino.

Particularly preferred are the following compounds:
7-[2-(Syn-methoxyimino)-2-(2-aminothiazol-4-yl)acetamido]-3-[4-amino-5-(1-pyrazolyl)-1,2,4-triazol-3-ylthiomethyl]-3-cephem-4-carboxylic acid;
7-[2-(Syn-methoxyimino)-2-(2-aminothiazol-4-yl)acetamido]-3-[4-amino-5-(1-[3,5-dimethyl]-pyrazolyl)-1,2,4-triazol-3-ylthiomethyl]-3-cephem-4-carboxylic acid;
7-[2-(Syn-methoxyimino)-2-(2-aminothiazol-4-yl)acetamido]-3-[4-amino-5-(1-[3-methyl-5-phenyl]-pyrazolyl)-1,2,4-triazol-3-ylthiomethyl]-3-cephem-4-carboxylic acid;
7-[2-(2-Thienyl)acetamido]-3-[4-amino-5-(1-pyrazolyl)-1,2,4-triazol-3-ylthiomethyl]-3-cephem-4-carboxylic acid;
7-[2-(Syn-methoxyimino)-2-(2-aminothiazol-4-yl)-acetamido]-3-[5-(1-pyrazolyl)-1,2,4-triazol-3-ylthiomethyl]-3-cephem-4-carboxylic acid;
7-[2-(4-Ethyl-2,3-dioxo-1-piperazinecaboxamido)-2-(p-hydroxyphenyl)acetamido]-3-[5-(1-pyrazolyl)-1,2,4-triazol-3-ylthiomethyl]-3-cephem-4-carboxylic acid;
7-[2-(4-Ethyl-2,3-dioxo-1-piperazinecarboxamido)-2-(p-hydroxyphenyl)acetamido]-3-[4-amino-5-(1-pyrazolyl)-1,2,4-triazol-3-ylthiomethyl]-3-cephem-4-carboxylic acid;
7-[2-(4-Ethyl-2,3-dioxo-1-piperazinecarboxamido)-2-(p-hydroxyphenyl)acetamido]-3-[4-amino-5-(3,5-dimethyl-1-pyrazolyl)-1,2,4-triazol-3-ylthiomethyl]-3-cephem-4-carboxylic acid;
7-D-(2-t-Butyloxycarbonylamino-2-phenylacetamido)-3-[5-(1-pyrazolyl)-1,2,4-triazol-3-ylthiomethyl]-3-cephem-4-carboxylic acid;
7-D-2-Amino-(2-phenylacetamido)-3-[5-(1-pyrazolyl)-1,2,4-triazol-3-ylthiomethyl]-3-cephem-4-carboxylic acid, trifluoroacetate salt; and
7-[2-(4-Ethyl-2,3-dioxo-1-piperazinecarboxamido)-2-(p-hydroxyphenyl)acetamido]-3-[4-amino-5-(1-[3-methyl-5-(2-thienyl]pyrazolyl)-1,2,4-triazol-3-ylthiomethyl]-3-cephem-4-carboxylic acid.

The compounds of the present invention may be prepared as indicated by the following diagram and description:

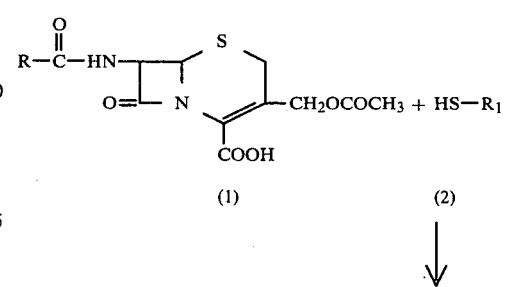

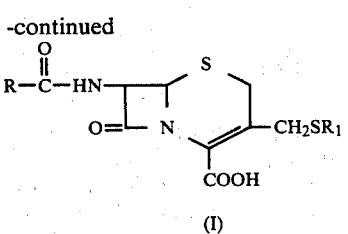

where R and R₁ are as previously defined.

A known cephalosporin (1) which has an acetoxy group in the three position, such as cephalothin or cephaloglycin, is reacted with an appropriate mercaptopyrazolyltriazole (2) where R₁ is as previously defined, in aqueous organic or inorganic base, e.g., sodium bicarbonate with sufficient inert organic solvent to produce solution for a time and temperature sufficient to effect the desired reaction, typically about 50°–70° for 6 to 18 hours. While any of a variety of inert organic solvents may be used, the solvents of preference are those polar solvents such as acetone. The amount of organic or inorganic base present in the reaction varies depending on the base strength of the actual base used. Sufficient base to effect the coupling reaction will be achieved at a pH of from about 6 to about 8. The reaction mixture is then acidified with a suitable mineral acid such as dilute hydrochloric acid and the product cephalosporin of formula I separated by convention techniques. Such techniques include extraction of the reaction solution with a suitable organic solvent, precipitating the product by chilling or various chromatographic techniques such as exemplified by the column, thin layer or paper chromatographic procedures.

As an alternative embodiment, the compounds of formula I are obtained by reacting compound (1) with the appropriate mercapto pyrazolyltriazole (2) in a polar solvent such as acetonitrile at 100°–200° C. for about 10 to about 40 hours. The solution is typically evaporated to obtain the product.

In the specification herein the term "$C_1$ to $C_6$ alkyl" is intended to mean those fully saturated monovalent radicals containing only carbon and hydrogen, such including both branched and linear aliphatic carbon chain of not more than 6 carbon atoms. Examples of such alkyl groups include methyl, ethyl, n-propyl, i-propyl, t-butyl, etc. The term "substituted phenyl" includes both mono and disubstituents on the phenyl group such as for example, $C_1$ to $C_3$ alkyl, $C_1$ to $C_3$ alkoxy, halo (fluoro, chloro and bromo), trifluoromethyl, etc. The term "heterocyclic aryl" includes the substituted and unsubstituted aromatic ring compounds of five or six members composed principally of carbon but including in such ring one, two or three members other than carbon such as nitrogen, oxygen, sulfur or mixtures thereof. Such hetero groups include 2- or 3-pyrroyl, 2- or 3-thienyl, 2- or 3-furyl, 2-, 4- or 5-oxazolyl, 3-, 4- or 5-isothiazolyl, 1,3,4-triazol-2-yl, etc. Substituents include those disclosed before for the term "substituted phenyl."

The compounds of the present invention are active antibacterial agents.

The compounds of Formula I may possess a chiral center. In some cases, one asymmetric may be more active than the opposite isomeric form. Accordingly, the compounds of this invention may be prepared in either their optically active form or as a racemic mixture. Unless otherwise specified, the compounds described herein are all in their racemic form. However, the scope of the subject invention is not to be considered limited to the racemic form, but to encompass the individual optical isomers of the compounds of the present invention.

When desired, the individual diastereometric and optically isomeric compounds can be isolated by conventional separation and purification procedures in the case of diastereoisomers and by conventional resolution procedures in the case of optical isomers. Optimal physical, or physical chemical separation procedures and resolution procedures can be obtained by routine trial and error procedures well within the scope of those skilled in the art.

A further understanding of the invention can be had from the following non-limiting preparations and examples. As used herein above and below, unless expressly stated to the contrary, all temperatures and temperature ranges referred to the centigrade system and the terms ambient to room temperature refer to about 20° C. The term percent or (%) refers to weight percent and the term mole and moles refers to gram moles. The term equivalent refers to a quantity of reagent equal in moles to the moles of the preceding or succeeding reactant recited in that preparation or example, in terms of moles of finite weight or volume. As noted earlier, compounds having asymmetric centers and optical activity are isolated in their racemic form (±) unless otherwise specified.

PREPARATIONS

4-Isopropylamino-3-mercapto-5-(1-pyrazolyl)-4H-1,2,3-triazole

4-Isopropylideneamino-3-mercapto-5-(1-pyrazolyl)-1,2,4-triazole (1.0 g) and 650 mg of sodium cyanoborohydride are stirred in 10 ml methanol at room temperature overnight. Methanol is evaporated the residue is washed with ethyl acetate and the ethyl acetate insoluble material is stirred with 5 ml of water. The pH is adjusted from 8.5 to 5.5. After extraction of the product with methylene chloride, the methylene chloride layer is washed with water and saturated sodium chloride, dried over magnesium sulfate and evaporated to an oil. The oil is stirred with 2 ml ether, chilled, and the ether is filtered off to give 540 mg, m.p. 80°–85° of the desired product.

PREPARATION 2

4-Isopropylideneamino-3-mercapto-5-(1-pyrazolyl)-1,2,4-triazole

4-Amino-3-mercapto-5-pyrazolyl-1,2,4-triazole (10 g) was refluxed in 1 liter of acetone and 0.5 ml triethylamine for 3 hours. Solids are filtered off and the filtrate is evaporated to dryness. The residue is extracted with 4×100 ml boiling ethyl ether. The ether is boiled to 50 ml and chilled at −20° C. to give 6.3 g of white crystals, m.p. 132°–8°, of 4-isopropylideneamino-3-mercapto-5-pyrazolyl-1,2,4-triazole.

Anal. Calcd for $C_8H_{10}N_6S$: C,43.2 H, 4.5 N, 37.8 S, 14.4. Found: C,43.2 H, 4.71 N, 37.81 S, 14.40.

PREPARATION 3

4-Amino-3-mercapto-5-[1-(3-methyl-5-hydroxy)-pyrazolyl]-1,2,4-triazole

4-Amino-5-hydrogen-3-mercapto-1,2,4-triazole (7.3 g, 0.05 mol), 5.8 g (0.005 mol) of methyl acetoacetate, and 4 ml concentrated hydrochloric acid are refluxed 4 hours in 500 ml of ethanol. After evaporation to 125 ml and chilling, 5.7 g of white crystals, m.p. 204°, of the desired product is filtered off and dried.

Anal: Calcd for C₆H₈N₆SO: C, 34.0 H, 3.8 N, 39.6 S, 15.1. Found: C, 33.79 H, 4.0 N, 38.4 S, 15.0.

PREPARATION 4

4-Amino-3-mercapto-5-(4,5,6,7-tetrahydro-3-methyl-1H-indazol-1-yl)-4H-1,2,4-triazole 4-Amino-5-hydrazino-3-mercapto-1,2,3-triazole (7.3 g, 0.05 mol), 7.0 g (0.05 mol) acetyl cyclohexanone, 1.25 ml concentrated hydrochloric acid, and 350 ml ethanol are refluxed for 3 hours, evaporated to dryness, and recrystallized from ethyl acetate to give 1.2 g of white crystals, m.p. 201°–2°.

PREPARATION 5

4-Amino-3-mercapto-5-[1-(3-trifluoromethyl-5-[2-thienyl])pyrazolyl]-1,2,4-triazole 4-Amino-5-hydrazino-3-mercapto-1,2,4-triazole (7.3 g, 0.05 mol) and 10.8 g (0.05 mol) 4,4,4-trifluoro-1-(2-thienyl)-1,3-butanedione are refluxed in 350 ml ethanol with 1.25 ml concentrated hydrochloric acid for 3 hours. The ethanol is evaporated and the residue is dissolved in 1 liter methylene chloride, filtered through Celite ® and chilled to yield 11.5 g, m.p. 160°–2°, of the desired product.

Anal: Calcd C₁₀H₇F₃N₆S: C, 36.1 H, 2.1 F, 17.2 N, 25.3. Found: C, 35.6 H, 2.1 F, 17.2 N, 25.2.

PREPARATION 6

4-Amino-3-mercapto-5-(1-pyrazolyl)-1,2,4-triazole

4-Amino-5-hydrazino-3-mercapto-1,2,4-triazole (14.1 g, 0.1 mol) and 16.4 g of malonaldehyde bis dimethyl acetal are refluxed in 200 ml ethanol with 1 ml of concentrated hydrochloric acid for 2 hours. The ethanol is evaporated and recrystallization from methanol yields 11.5 g of off white crystals, m.p. 180° (dec).

PREPARATION 7

3-mercapto-5(1-pyrazolyl)-1,2,4-triazole

Sodium nitrite (0.4 g) was added to 25 ml of conc HNO₃ and 75 ml H₂O (after R. A. Henry and W. G. Finnegan, J. Am. Chem. Soc., 76, 290 (1954) and C. A. Amsworth and R. G. Jones J. Am. Chem. Soc., 75, 4915 (1953). Solid 4-amino-3-mercapto-5-(1-pyrazolyl)-1,2,4-triazole (5 g) was added in small batches with stirriing while keeping the temperature below 40° C. After addition, the solution was stirred for 20 minutes and made basic by the addition of 15% aq. Na₂CO₃. The yellow solution was filtered and acidified with glacial acetic acid (25 ml). The tan precipitate was collected and boiled with ethanol to give 2.3 g of tan powder m.p. 245°–247°.

PREPARATION 8

4-Amino-3-mercapto-5-[1-(3-trifluoromethyl-5-ethoxy)-pyrazolyl]-1,2,4-triazole

A mixture of 3.65 g (0.025 mol) 4-amino-5-hydrazino-3-mercapto-1,2,4-triazole, 4.6 g (0.025 mol) of ethyl 4,4,4-trifluoroacetoacetate, 200 ml ethanol, and 1 ml concentrated hydrochloric acid are refluxed overnight. Ethanol is boiled off to a volume of 75 ml and the solution is chilled to give 4.2 g of white crystals, m.p. 165°–9°.

PREPARATION 9

4-Amino-3-mercapto-5-[1-(3-methyl-5-[2-thienyl])pyrazolyl]-1,2,4-triazole

A mixture of 2.9 (0.02 mol) 4-amino-5-hydrazino-3-mercapto-1,2,3-triazole, 3.4 g of 1-thienyl-1,3-butanedione, 0.5 ml concentrated hydrochloric acid, and 140 ml ethanol are refluxed for 5 hours. The solution is evaporated to 20 ml, chilled, and the light yellow crystalline solid is collected by filtration. Recrystallization from methylene chloride affords 2.95 g, m.p. 188°, of the desired product as a white, crystalline solid.

Anal: Calcd for C₁₀H₁₀N₆S₂: C, 43.2 H, 3.6 N, 30.2 S, 23.0. Found: C, 42.9 H, 3.6 N, 30.0 S, 23.4.

PREPARATION 10

4-Amino-3-mercapto-5-[1-(3-methyl-5-[2-furyl])pyrazolyl]-1,2,4-triazole

4-Amino-3-mercapto-5-hydrazino-1,2,4-triazole (7.3 g, 0.5 mole), 7.6 g (0.5 mol) of 1-(2-furyl)-1,3-butanedione, 1.25 ml concentrated hydrochloric acid, and 300 ml of ethanol are refluxed for 3 hours, evaporated to 150 ml, and chilled to give 9.0 g of yellow crystals, m.p. 193°–40°.

Anal: Calcd for C₁₀H₁₀N₆OS: C, 45.8 H, 3.8 N, 32.1 S, 12.2. Found: C, 45.7 H, 3.9 N, 32.0 S, 12.3.

PREPARATION 11

4-Amino-3-mercapto-5-[1-(3,5-dimethyl)pyrazolyl]-1,2,4-triazole

A mixture of 4.4 g (0.03 mol) 4-amino-3-hydrazino-5-mercapto-1,2,4-triazole and 3.0 g of 2,4-pentanedione in 250 ml ethanol plus 0.5 ml of concentrated hydrochloric acid was refluxed overnight. Ethanol was evaporated to a volume of 80 ml. The solution when chilled yielded 4 g of yellow crystals, m.p. 179°–181°.

PREPARATION 12

4-Amino-3-mercapto-5-[1-(3-methyl-5-phenyl)-pyrazolyl)-1,2,4-triazole

4-Amino-5-hydrazino-3-mercapto-1,2,4-triazole (4.4 g, 0.3 mol), 4.8 g (0.3 mol) of 1-benzoylacetone, 0.5 ml of concentrated hydrochloric acid, and 200 ml of ethanol are refluxed overnight. Ethanol is evaporated to 50 ml and the solution chilled to give 4.2 g of off-white crystals, m.p. 200°–202°.

EXAMPLES

The compounds of this invention may be physically characterized and their purity determined by any or all of the following methods: Thin layer chromatography (t.l.c.), infrared spectroscopy (i.r.), nuclear magnetic resonance spectroscopy (n.m.r.) and high pressure liquid chromatography (h.p.l.c.).

In the i.r. (potassium bromide disc) these compounds have a characteristic β-lactam peak at 5650 nm.

EXAMPLE 1

7-[2-(Syn-methoxyimino)-2-(2-aminothiazol-4-yl)acetamido]-3-[4-amino-5-(1-pyrazolyl)-1,2,4-triazol-3-ylthiomethyl]-3-cephem-4-carboxylic acid A solution of 495 mg. of 7-[2-syn-(methoxyimino)(2-aminothiazol-4-yl)acetamido]cephalosporanic acid, sodium salt and 984 mg. of sodium bicarbonate in 20 ml. of water is treated with 200 mg. of 4-amino-3-mercapto-5-(1-pyrazolyl)-1,2,4-triazole. A 4 ml. portion of acetone is added to achieve solution. The solution is stirred at 60° C. for 11 hours at a constant pH of 7, then cooled to room temperature and adjusted to pH 5.5 with 1 N hydrochloric acid. The mixture is extracted with ethyl acetate. The aqueous layer is adjusted to pH 3 and then chilled in an ice bath. The resulting precipitate is filtered, washed with water and dried, giving 350 mg. of the desired product as an off-white solid.

$\lambda_{max}^{KBr}$: 5650 nm ($\beta$-lactam).

nmr (d$_6$-DMSO): 3.84 $\delta$(S) (=N—OCH$_3$); 6.65 $\delta$(m) (pyrazole H); 6.75 $\delta$(S) (thiazole H5); 7.94 $\delta$(pyrazole H4); 8.37 $\delta$(d, pyrazole H).

EXAMPLE 2

7-[2-(Syn-methoxyimino)-2-(2-aminothiazol-4-yl)acetamido]-3-[4-amino-5-(1-[3,5-dimethyl]-pyrazolyl)-1,2,4-triazol-3-ylthiomethyl]-3-cephem-4-carboxylic acid A solution of 495 mg. of 7-[2-syn-(methoxyimino)-(2-aminothiazol-4-yl)acetamido]cephalosporanic acid, sodium salt and 84 mg. of sodium bicarbonate in 20 ml. of water is reacted with 231 mg. of 4-amino-3-mercapto-5-[1-(3,5-dimethyl)pyrazolyl]-1,2,4-triazole for 12 hours as described in Example 1, giving 200 mg. of the desired product as an off-white solid.

$\lambda_{max}^{KBr}$: 5650 nm ($\beta$-lactam).

nmr (d$_6$-DMSO): 2.23 $\delta$(S) and 2.29 $\delta$(S) (pyrazole-CH$_3$); 3.86 $\delta$(S) (=N—OCH$_3$); 6.72 $\delta$(thiazole H5).

EXAMPLE 3

7-[2-(Syn-methoxyimino)-2-(2-aminothiazol-4-yl)acetamido]-3-[4-amino-5-(1-[3-methyl-5-phenyl]-pyrazolyl)-1,2,4-triazol-3-ylthiomethyl]-3-cephem-4-carboxylic acid A solution of 490 mg. of 7-[2-syn-(methoxyimino)-(2-aminothiazol-4-yl)acetamido]cephalosporanic acid, sodium salt and 84 mg. of sodium bicarbonate in 20 ml. of water is reacted with 299 mg. of 4-amino-3-mercapto-5-[1-(3-methyl-5-phenyl)pyrazolyl]-1,2,4-triazole as described in Example 1, giving 450 mg. of the desired product as an off-white solid.

$\lambda_{max}^{KBr}$: 5650 mnm ($\beta$-lactam).

nmr (d$_6$-DMSO): 2.32 $\delta$ (S) (pyrazole-CH$_3$); 3.87 $\delta$(S) (=N—OCH$_3$); 6.71 $\delta$ (S) (thiazole H5); 7.37 $\delta$(S) (phenyl).

EXAMPLE 4

7[2-(2-Thienyl)acetamido]-3-[4-amino-5-(1-pyrazolyl)-1,2,4-triazol-3-ylthiomethyl]-3-cephem-4-carboxylic acid A solution of 400 mg. of the sodium salt of 7-[2-(2-thienyl)acetamido]cephalosporanic acid in 5 ml. of pH 6.4 phosphate buffer is stirred for 12 hours at 60° C. with 270 mg. of 4-amino-3-mercapto-5-(1-pyrazolyl)-1,2,4-triazole with the addition of sufficient acetone to produce solution. The solution is cooled to room temperature, 10 ml. of water is added, the pH is adjusted to 5.5 and the solution is extracted with ethyl acetate. The aqueous layer is adjusted to pH 2.5 and extracted with several portions of ethyl acetate. The combined ethyl acetate extracts are washed with water, then saturated aqueous sodium chloride, dried over magnesium sulfate and evaporated, giving 165 mg. of the desired product as a white solid.

$\lambda_{max}^{KBr}$: 5650 nm ($\delta$-lactam).

nmr (d$_6$-DMSO): 6.61 $\delta$(m), 7.88 $\delta$(S), 8.30 $\delta$(m) (pyrazole H'S); 6.94 $\delta$(m) (2H), 7.30 $\delta$(1H) (thiophene H'S).

EXAMPLE 5

7-[2-(Syn-methoxyimino)-2-(2-aminothiazol-4-yl)-acetamido]-3-[5-(1-pyrazolyl)-1,2,4-triazol-3-ylthiomethyl]-3-cephem-4-carboxylic acid A solution of 477.5 mg. of 7-[2-syn-(methoxyimino) (2-aminothiazol-4-yl)acetamido]cephalosporanic acid sodium salt and 185.5 mg. of 5-(1-pyrazolyl)-4H-1,2,4-triazole-3-thiol in 15 ml. of water and 0.73 ml. of 1.5 M sodium bicarbonate solution is stirred and heated at 60° C. for 8 hours. The mixture is centrifuged until clear and then acidified to pH 2.5 with concentrated hydrochloric acid. The mixture is cooled in ice for one hour and the resulting precipitate is filtered and dried, giving 400 mg. of the desired product.

EXAMPLE 6

7-[2-(4-Ethyl-2,3-dioxo-1-piperazinecarboxamido)-2-(p-hydroxyphenyl)acetamido]-3-[5-(1-pyrazolyl)-1,2,4-triazol-3-ylthiomethyl]-3-cephem-4-carboxylic acid A suspension of 147.4 mg. of 7-[2-(4-ethyl-2,3-dioxo-1-piperazinecarboxamido)-2-(p-hydroxyphenyl)acetamido]-3-hydroxymethyl-8-oxo-5-thia-1-azabicyclo[4.2.0]-oct-2-ene-2-carboxylic acid, 3-acetate and 62.7 mg. of 5-(1-pyrazolyl)-4H-1,2,4-triazole-3-thiol in 10 ml. of water is adjusted to pH 6.5 with an aqueous solution of sodium bicarbonate. The mixture is stirred at 60° C. for 5 hours, then cooled to room temperature and filtered. The filtrate is acidified to pH 2.0 with 2 N hydrochloric acid and the resulting solid is filtered, washed with water and dried, giving 65 mg. of the desired product as a light yellow solid.

EXAMPLE 7

7-[2-(4-Ethyl-2,3-dioxo-1-piperazinecarboxamido)-2-(p-hydroxyphenyl)acetamido]-3-[4-amino-5-(1-pyrazolyl)-1,2,4-triazol-3-ylthiomethyl]-3-cephem-4-carboxylic acid A suspension of 294.78 mg. of 7-[2-(4-ethyl-2,3-dioxo-1-piperazinecarboxamido)-2-(p-hydroxyphenyl)acetamido]-3-(hydroxymethyl)-8-oxo-5-thia-1-azabicyclo[4.2.0]-oct-2-ene-2-carboxylic acid, 3-acetate and 136.6 mg. of 4-amino-5-(1-pyrazolyl)-4H-1,2,4-triazole-3-thiol in 10 ml. of water is adjusted to pH 6.5 with an aqueous solution of sodium bicarbonate. A 5 ml. portion of acetone is added producing solution. This solution is stirred at 60°-63° C. for 5 hours, then stripped free of acetone under reduced pressure, cooled to room temperature and filtered. The filtrate is acidified to pH 2.0 with 2 N hydrochloric acid. The resulting solid is filtered and dried giving 192 mg. of the desired product.

EXAMPLE 8

7-[2-(4-Ethyl-2,3-dioxo-1-piperazinecarboxamido)-2-(p-hydroxyphenyl)acetamido]-3-[4-amino-5-(3,5-dimethyl-1-pyrazolyl)-1,2,4-triazol-3-ylthiomethyl]-3-cephem-4-carboxylic acid A suspension of 294.78 mg. of 7-[2-(4-ethyl-2,3-dioxo-1-piperazinecarboxamido)-2-(p-hydroxyphenyl)acetamido]-3-(hydroxymethyl)-8-oxo-5-thia-1-azabicyclo[4.2.0]-oct-2-ene-2-carboxylic acid, 3-acetate and 157.7 mg. of 4-amino-5-(3,5-dimethyl-1-pyrazolyl)-4H-1,2,4-triazole-3-thiol in 10 ml. of water is adjusted to pH 6.5 with aqueous sodium carbonate. A 2 ml. portion of acetone is added producing solution. This solution is stirred at 60°–63° C. for 5½ hours, then stripped free of acetone under reduced pressure and acidified to pH 2.0 with 2 N hydrochloric acid. The resulting solid is filtered, washed repeatedly with ethyl acetate, then with ether and dried, giving 190 mg. of the desired product as a yellow solid.

EXAMPLE 9

7-(D-2-t-Butyloxycarbonylamino-2-phenylacetamido)-3-[5-(1-pyrazolyl)-1,2,4-triazol-3-ylthiomethyl]-3-cephem-4-carboxylic acid A suspension of 350 mg. of 7-(D-2-t-butyloxycarbonylamino-2-phenylacetamido-3-acetoxymethyl-3-cephem-4-carboxylic acid ester and 150 mg. of 5-(1-pyrazolyl)-4H-1,2,4-triazole-3-thiol in 5 ml. of acetonitrile is refluxed for 24 hours, then kept at 25° C. for 16 hours. The mixture is filtered and the filtrate is evaporated, giving 359 mg. of the desired product.

$\lambda_{max}^{KBr}$: 5.63 nm ($\beta$-lactam).

EXAMPLE 10

7-(D-2-Amino-2-phenylacetamido)-3-[5-(1-pyrazolyl)-1,2,4-triazol-3-ylthiomethyl]-3-cephem-4-carboxylic acid, trifluoroacetate salt A solution of 200 mg. of 7-(D-2-carboxyamino-2-phenylacetamido)-3-(acetoxymethyl)-8-oxo-5-thia-1-azabicyclo[4.2.0]oct-2-ene-2-carboxylic acid, 7-t-butyl ester in 2 ml. of cold trifluoroacetic acid is kept in an ice bath for 5 minutes and poured into excess ether, giving 144 mg. of the desired product.

$\lambda_{max}^{KBr}$: 5.63 nm ($\beta$-lactam).

EXAMPLE 11

7-[2-(4-Ethyl-2,3-dioxo-1-piperazinecarboxamido)-2-(p-hydroxyphenyl)acetamido]-3-[4-amino-5-(1-[3-methyl-5-(2-thienyl]pyrazolyl)-1,2,4-triazol-3-ylthiomethyl]-3-cephem-4-carboxylic acid A suspension of 294.78 mg. of 7[2-(4-ethyl-2,3-dioxo-1-piperazinecarboxamido)-2-(p-hydroxyphenyl)acetamido]-3-(hydroxymethyl)-8-oxo-5-thia-1-azabicyclo[4.2.0]oct-2-ene-2-carboxylic acid, 3-acetate and 208.77 mg. of 4-amino-5[3-methyl-5-(2-thienyl)-1-pyrazolyl]-4H-1,2,4-triazole-3-thiol in 10 ml. of water is adjusted to pH 6.5 with aqueous sodium bicarbonate. A 3 ml. portion of acetone is added producing a solution. This solution is stirred at 60°–65° C. for 7 hours, then stripped free of acetone under reduced pressure and extracted with 50 ml. of ethyl acetate. The aqueous phase is acidified to pH 2.0 with 2 N hydrochloric acid. The resulting solid is filtered, washed repeatedly with water, then with ether and dried, giving 160 mg. of the desired product as a light yellow solid.

EXAMPLE 12

7-[2-(syn-Methoxyimino)-2-(2-aminothiazol-4-yl)acetamido]-3-[4-amino-5-(1-[3-methyl-5-(2-thienyl]-pyrazolyl)-1,2,4-triazol-3-ylthiomethyl]-3-cephem-4-carboxylic acid A solution of 260 mg (0.5 mmol) of 7-[2-syn-(methoxyimino)-2-(2-aminothiazol-4-yl)acetamido]cephalosporanic acid, formic acid salt and 126 mg of sodium bicarbonate in 10 ml water is reacted with 153 mg of 4-amino-3-mercapto-5-[1-(3-methyl-5-[2-thienyl]-)pyrazolyl]-1,2,4-triazole for 12 hours as described in Example 1, giving 110 mg of the desired product as an off white solid.

EXAMPLE 13

7-[2-(syn-Methoxyimino-2-(2-aminothiazol-4-yl)acetamido]-3-[4-amino-5-(1-[3-trifluoromethyl-5-(2-thienyl)]-pyrazolyl)-1,2,4-triazol-3-yl-thiomethyl]-3-cephem-4-carboxylic acid A solution of 260 mg (0.5 mmol) of 7-[2-syn-(methoxyimino)-(2-aminothiazol-4-yl)acetamido]cephalosporanic acid, formic acid salt and 126 mg of sodium bicarbonate in 10 ml of water is reacted with 183 mg of 4-amino-3-mercapto-[1-(3-trifluoromethyl-5-(2-thienyl)]-1,2,4-triazole for 24 hours as described in Example 1, giving 105 mg of the desired product as an off white solid.

EXAMPLE 14

7-[2-syn-Methoxyimino)-2-(2-aminothiazol-4-yl)acetamido]3,[4-amino-5-(1-[3-methyl-5-hydroxy]-pyrazolyl)-1,2,4-triazol-3-ylthiomethyl]-3-cephem-4-carboxylic acid Reaction of 260 mg (0.5 mmol) of 7-[2-syn-(methoxyimino)-2-(2-aminothiazol-4-yl)acetamido]cephalosporanic acid, formic acid salt, 116 mg (0.55 mmol) of 4-amino-3-mercapto-5-[1-(3-methyl-5-hydroxy)-pyrazolyl]-1,2,4-triazole, and 126 mg sodium bicarbonate in 10 ml water for 12 hours according to the procedure in Example 1 gives 230 mg of the desired product as a light pink solid.

EXAMPLE 15

7-[2-(syn-Methoxyimino)-2-(2-aminothiazol-4-yl)acetamido]-3-[4-amino-5-(1-[3-trifluoromethyl-5-ethoxy]pyrazolyl)-1,2,4-triazol-3-ylthiomethyl]-3-cephem-4-carboxylic acid Reaction of 260 mg (0.5 mmol) of 7-[2-syn-(methoxyimino)-2-(2-aminothiazol-4-yl)acetamido]cephalosporanic acid, formic acid salt, 162 mg 10.55 mmol) of 4-amino-3-mercapto-5-[1-(3-trifluoromethyl-5-ethoxy)-pyrazolyl]-1,2,4-triazole, and 126 mg of sodium bicarbonate in 10 ml water for 12 hours according to the procedure in Example 1 gives 123 mg of the desired product as a light yellow solid.

EXAMPLE 16

7-[2-(syn-Methoxyimino-2-(2-aminothiazol-4-yl)acetamido]-3-[4-amino-5-(3-methyl-4,5,6,7-tetrahydroindazol-1-yl)-1,2,4-triazol-3-ylthiomethyl]-3-cephem-4-carboxylic acid When 260 mg (0.5 mmol) of 7-[2-syn-methoxyimino)-2-(2-aminothiazol-4-yl)acetamido]cephalosporanic acid, formic acid salt, 137 mg (0.55 mmol) of 4-amino-3-mercapto-5-[3-methyl-4,5,6,7-tetrahydroindazol-1-yl]-1,2,4-triazole and 126 mg of sodium bicarbonate are reacted in 10 ml water for 12 hours as described in Example 1, giving 160 mg of the desired product is obtained as a light yellow solid.

EXAMPLE 17

7-[2-syn-Methoxyimino)-2-(2-aminothiazol-4-yl)acetamido]-3-[4-amino-5-(1-[3-methyl-5-(2-furyl)-]pyrazolyl)-1,2,4-triazol-3-ylthiomethyl]-3-cephem-4-carboxylic acid Reaction of 260 mg (0.5 mmol) of 7-[2-syn-(methoxyimino)-(2-aminothiazol-4-yl)acetamido]cephalosporanic acid, formic acid salt, 144 mg (0.55 mmol) of 4-amino-3-mercapto-5-[1-(3-methyl-5-[2-furyl])pyrazolyl]-1,2,4-triazole, and 126 mg sodium bicarbonate in 10 ml water for 12 hours as described in Example 1, gives 145 mg of the desired product as an off white solid.

EXAMPLE 18

7-[2-syn-Methoxyimino)-2-(2-aminothiazol-4-ylacetamido]-3-[4-isopropylamino-5-(1-pyrazolyl)-1,2,4-triazol-3-ylthiomethyl]-3-cephem-4-carboxylic acid Reaction of 260 mg (0.5 mmol) of 7-[2-syn-(methoxyimino)-(2-aminothiazol-4-yl)acetamido]-cephalosporanic acid, formic acid salt, 136 mg (0.55 mmol) of 4-isopropylamino-3-mercapto-5-(1-pyrazolyl)-1,2,4-triazole, and 126 mg of sodium bicarbonate in 10 ml water for 16 hours according to the procedure in Example 1, affords 200 mg of the desired product as an off white solid.

EXAMPLE 19

The in vitro activity of representative compounds of the present invention are given in the following Table I in terms of minimal inhibitory concentration. The test used was the standard agar dilution test using a Steers multiple inocula replicator and incubating at 35° C. for 18 hours in conventional nutrient agar.

EXAMPLE 20

The usefulness of the antibacterial agents of the present invention is demonstrated by their ability to control systemic lethal infections. As shown in Table II these compounds show high in vivo antibacterial activity against *Escherichia coli* 311 and *Klebsiella pneumoniae* W-75-2 when administered by a single subcutaneous dose to groups of Charles River CD-1 mice, weighing about 20 g. each. The mice are infected intraperitoneally with a lethal dose of these bacteria.

In Table II the compounds are coded the same as in Table I.

The compounds in Table I are coded as follows:

| Compound I | 7-[2-(Syn-methoxyimino)-2-(2-aminothiazol-4-yl)acetamido]-3-[4-amino-5-(1-pyrazolyl)-1,2,4-triazol-3-ylthiomethyl]-3-cephem-4-carboxylic acid |
| Compound II | 7-[2-(Syn-methoxyimino)-2-(2-aminothiazol-4-yl)acetamido]-3-[4-amino-5-(1-[3,5-dimethyl]-pyrazolyl)-1,2,4-triazol-3-ylthiomethyl]-3-cephem-4-carboxylic acid |
| Compound III | 7-[2-(Syn-methoxyimino)-2-(2-aminothiazol-4-yl)acetamido]-3-[4-amino-5-(1-[3-methyl-5-phenyl]pyrazolyl)-1,2,4-triazol-3-ylthiomethyl]-3-cephem-4-carboxylic acid |
| Compound IV | 7-[2-(2-Thienyl)acetamido]-3-[4-amino-5-(1-pyrazolyl)-1,2,4-triazol-3-ylthiomethyl]-3-cephem-4-carboxylic acid |
| Compound V | 7-[2-Syn-methoxyimino)-2-(2-aminothiazol-4-yl)acetamido]-3-[5-(1-pyrazolyl)-1,2,4-triazol-3-ylthiomethyl]-3-cephem-4-carboxylic acid |
| Compound VI | 7-[2-(4-Ethyl-2,3-dioxo-1-piperazinecarboxamido)-2-(p-hydroxyphenyl)acetamido]-3-[5-(1-pyrazolyl)-1,2,4-triazol-3-ylthiomethyl]-3-cephem-4-carboxylic acid |
| Compound VIII | 7-[2-(4-Ethyl-2,3-dioxo-1-piperazinecarboxamido)-2-(p-hydroxyphenyl)acetamido]-3-[4-amino-5-(1-pyrazolyl)-1,2,4-triazol-3-ylthiomethyl]-3-cephem-4-carboxylic acid |
| Compound VIII | 7-[2-(4-Ethyl-2,3-dioxo-1-piperazinecarboxamido)-2-(p-hydroxyphenyl)acetamido]-3-[4-amino-5-(3,5-dimethyl-1-pyrazolyl)-1,2,4-triazol-3-ylthiomethyl]-3-cephem-4-carboxylic acid |
| Compound IX | 7-(D-2-Amino-2-phenylacetamido)-3-[5-(1-pyrazolyl)-1,2,4-triazol-3-ylthiomethyl]-3-cephem-4-carboxylic acid, trifluoroacetate salt |
| Compound X | Caphalothin (comparative) |
| Compound XI | Cephaloglycin (Comparative) |
| Compound XII | Cefazolin (comparative) |

TABLE I

In vitro Activity Expressed as Minimal Inhibitory Concentration in mcg./ml.

| Organism Name and Number | I | II | III | IV | V | VI | VII | VIII | IX | X | XI | XII |
|---|---|---|---|---|---|---|---|---|---|---|---|---|
| *Pseudomonas aeruginosa* G236 | 64 | 128 | >128 | >128 | 16 | 32 | 32 | 128 | >128 | >128 | >128 | >128 |
| *Pseudomonas aeruginosa* PD05141 | 128 | >128 | >128 | >128 | 64 | 64 | 64 | >128 | >128 | >128 | >128 | >128 |
| *Pseudomonas aeruginosa* 12-4-4 | 64 | 64 | 128 | >128 | 16 | 16 | 16 | 32 | >128 | >128 | >128 | >128 |
| *Pseudomonas aeruginosa* UCS 76-13 | 128 | >128 | >128 | >128 | 64 | 64 | 64 | >128 | >128 | >128 | >128 | >128 |
| *Klebsiella pneumoniae* MA75-1 | ≦0.12 | ≦0.12 | 0.5 | 2 | ≦0.12 | 2 | 1 | 2 | 16 | 1 | 1 | 1 |
| *Klebsiella pneumoniae* W75-2 | ≦0.12 | 0.25 | 1 | 2 | ≦0.12 | 4 | 2 | 4 | 32 | 2 | 2 | 1 |
| *Klebsiella pneumoniae* W75-4 | ≦0.12 | 0.25 | 1 | 16 | ≦0.12 | 32 | 32 | 32 | 32 | 8 | 8 | 16 |
| *Klebsiella pneumoniae* UR76-1 | 0.5 | 0.5 | 4 | >128 | 0.25 | 16 | 16 | 32 | >128 | 8 | 16 | 64 |
| *Klebsiella pneumoniae* AD | ≦0.12 | ≦0.12 | 0.5 | 4 | ≦0.12 | 0.5 | 1 | 2 | 8 | 2 | 0.5 | 0.5 |
| *Enterobacter aerogenes* UR76-3 | ≦0.12 | ≦0.12 | 0.25 | 1 | ≦0.12 | 0.5 | 0.25 | 1 | 16 | 2 | 2 | 2 |
| *Enterobacter cloacae* MA75-1 | 128 | 128 | 128 | >128 | >128 | >128 | >128 | >128 | >128 | >128 | >128 | >128 |
| *Enterobacter cloacae* OSU75-2 | 0.5 | 2 | 4 | >128 | 4 | 64 | 16 | 128 | >128 | >128 | >128 | >128 |
| *Serratia* K101 | 0.5 | 1 | 4 | >128 | 0.5 | 128 | 32 | 64 | >128 | >128 | >128 | >128 |
| *Serratia marcens* K77-1 | 0.5 | 1 | 4 | >128 | 0.5 | >128 | 64 | 128 | >128 | >128 | >128 | >128 |
| *Serratia marcens* QHC77-2 | 1 | 2 | 8 | >128 | 0.25 | >128 | 128 | 128 | >128 | >128 | >128 | >128 |
| *Proteus vulgaris* N74-1 | ≦0.12 | 0.5 | 1 | — | 2 | 16 | 32 | 128 | >128 | — | >128 | >128 |
| *Proteus morganii* K72 | ≦0.12 | 0.5 | 2 | >128 | ≦0.12 | 32 | 32 | 32 | >128 | >128 | >128 | >128 |
| *Proteus rettgeri* N76-1 | ≦0.12 | 0.5 | 1 | >128 | ≦0.12 | 16 | 8 | 16 | >128 | >128 | >128 | >128 |
| *Escherichia coli* ESS22-31 | ≦0.12 | ≦0.12 | ≦0.12 | ≦0.06 | ≦0.12 | ≦0.12 | ≦0.12 | ≦0.12 | ≦0.12 | ≦0.06 | 0.12 | 0.25 |
| *Escherichia coli* W75-1 | ≦0.12 | 0.25 | 1 | 8 | ≦0.12 | 2 | 1 | 4 | 16 | 8 | 2 | 1 |
| *Escherichia coli* OSU75-1 | ≦0.12 | 0.25 | 1 | 4 | ≦0.12 | 2 | 1 | 4 | 16 | 8 | 2 | 1 |
| *Escherichia coli* 311 | ≦0.12 | ≦0.12 | 0.25 | 4 | ≦0.12 | 1 | 0.5 | 2 | 16 | 4 | 2 | 0.5 |
| *Staphylococcus aureus* Q74-1 | 2 | 2 | 2 | ≦0.12 | 1 | 4 | 2 | 4 | 4 | ≦0.06 | 1 | 0.12 |
| *Staphyloccocus aureus* Q74-6 | 64 | 64 | 32 | 0.25 | 64 | 8 | 4 | 8 | 1 | 0.12 | 0.12 | ≦0.06 |
| *Enterococcus* SM77-15 | >128 | >128 | >128 | 32 | >128 | 128 | 128 | 128 | >128 | 32 | 64 | 16 |

TABLE II

| Compound Number | Single Subcutaneous Dose (mg./kg.) | Alive/Total Mice Tested, Days After Infection | |
|---|---|---|---|
| | | Escherichia coli 311 | Klebsiella pneumoniae W-75-2 |
| I | 1 | 19/20 | |
| | 0.5 | 15/20 | 19/20 |
| | 0.25 | 6/20 | 14/20 |
| | 0.12 | 1/20 | 2/20 |
| | 0.06 | | 1/20 |
| II | 8 | 5/5 | |
| | 4 | 5/5 | |
| | 2 | 5/5 | |
| | 1 | 0/5 | |
| III | 8 | 5/5 | |
| | 4 | 5/5 | |
| | 2 | 0/5 | |
| | 1 | 0/5 | |
| V | 4 | 5/5 | |
| | 2 | 5/5 | |
| | 1 | 5/5 | |
| | 0.5 | 0/5 | |
| | 0.25 | 0/5 | |
| Cefamandol (comparison) | 32 | 20/20 | |
| | 16 | 20/20 | |
| | 8 | 11/20 | 20/20 |
| | 4 | 6/20 | 19/20 |
| | 2 | | 7/20 |
| | 1 | | 1/20 |
| | 0.5 | | 0/20 |

Having now fully described the invention, it will be apparent to one of ordinary skill in the art that many changes and modifications can be made thereto without departing from the spirit or scope of the invention as set forth herein.

We claim:

1. A compound of the formula

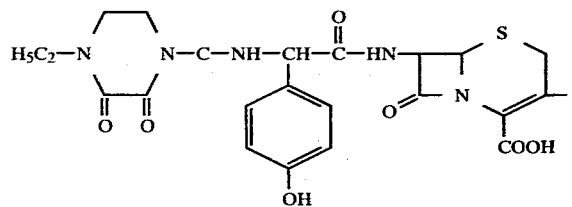

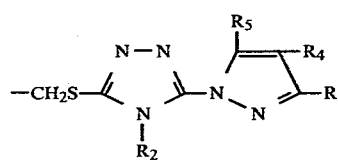

wherein
$R_2$ is selected from the group hydrogen, amino, $C_1$–$C_6$ alkylamino and di-$C_1$–$C_6$ alkylamino;
$R_3$, $R_4$, and $R_5$ are the same or different and are selected from the group hydrogen, hydroxy, $C_1$–$C_6$ alkyl, $C_1$–$C_6$ alkoxy, trifluoromethyl, phenyl, substituted phenyl, heterocyclic aryl, and $R_3$ and $R_4$ or $R_4$ and $R_5$ taken together are the moiety —$CH_2$—($CH_2$)$_2$—$CH_2$—;
wherein the substituents on the phenyl are mono- or di-substituents which are the same or different and which are selected from the group $C_1$–$C_3$ alkyl, $C_1$–$C_3$ alkoxy, fluoro, chloro, bromo, and trifluoromethyl; and
wherein the heterocyclic aryl is selected from the group of five- and six-membered aromatic ring compounds containing one to three heteroatoms which are the same or different and which are selected from the group oxygen, nitrogen, and sulfur, and wherein said heterocyclic aryl is optionally substituted as defined above for substituted phenyl;
and the pharmaceutically acceptable non-toxic salts thereof.

2. The compounds in accordance with claim 1 wherein $R_3$, $R_4$, and $R_5$ are the same or different and are selected from the group hydrogen; $C_1$–$C_6$ alkyl; phenyl; phenyl substituted with mono- or di-methyl, methoxy, chloro, bromo, or trifluoromethyl; thienyl; and pyrroyl; and $R_2$ is as previously defined.

3. The compounds in accordance with claim 2 wherein $R_3$, $R_4$, and $R_5$ are different and are individually selected from the group hydrogen, 3-methyl, 3-phenyl, 3-thien-2-yl, 3,5-dimethyl, 3-methyl-5-phenyl, and 3-methyl-5-thien-2-yl, and $R_2$ is as previously defined.

4. The compounds in accordance with claim 3 wherein $R_2$ is amino.

5. The compound in accordance with claim 4 that is 7-[2-(4-ethyl-2,3-dioxo-1-piperazinecarboxamido)-2-(p-hydroxyphenyl)acetamido]-3-[4-amino-5-(1-[3-methyl-5-(2-thienyl)]pyrazolyl)-1,2,4-triazol-3-ylthiomethyl]-3-cephem-4-carboxylic acid.

6. The compound in accordance with claim 4 that is 7-[2-(4-ethyl-2,3-dioxo-1-piperazinecarboxamido)-2-(p-hydroxyphenyl)acetamido]-3-[4-amino-5-(3,5-dimethyl-1-pyrazolyl)-1,2,4-triazol-3-ylthiomethyl]-3-cephem-4-carboxylic acid.

7. The compounds in accordance with claim 2 wherein $R_3$, $R_4$, and $R_5$ are the same and are hydrogen and $R_2$ is selected from the group hydrogen and amino.

8. The compound according to claim 7 that is 7-[2-(4-ethyl-2,3-dioxo-1-piperazinecarboxamido)-2-(p-hydroxyphenyl)acetamido]-3-[5-(1-pyrazolyl)-1,2,4-triazol-3-ylthiomethyl]-3-cephem-4-carboxylic acid.

9. The compound according to claim 7 that is 7-[2-(4-ethyl-2,3-dioxo-1-piperazinecarboxamido)-2-(p-hydroxyphenyl)-acetamido]-3-[4-amino-5-(1-pyrazolyl)-1,2,4-triazol-3-ylthiomethyl]-3-cephem-4-carboxylic acid.

* * * * *

UNITED STATES PATENT OFFICE
CERTIFICATE OF CORRECTION

Patent No. 4,404,375                    Dated September 13, 1983

Inventor(s) JAMES H. BOOTHE and ADMA S. ROSS

It is certified that error appears in the above-identified patent and that said Letters Patent are hereby corrected as shown below:

Claim 1, Col. 15, Line 39 should read:

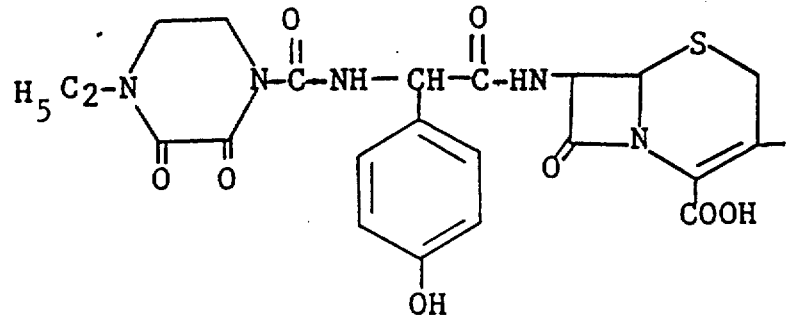

Signed and Sealed this

Fourth Day of June 1985

[SEAL]

Attest:

DONALD J. QUIGG

Attesting Officer        Acting Commissioner of Patents and Trademarks